United States Patent [19]

Lopez-Berestein et al.

[11] Patent Number: 4,978,654

[45] Date of Patent: Dec. 18, 1990

[54] COMPOSITION AND METHOD FOR TREATMENT OF DISSEMINATED FUNGAL INFECTIONS IN MAMMALS

[75] Inventors: Gabriel Lopez-Berestein; Victor Fainstein, both of Houston, Tex.; Evan M. Hersh, Tucson, Ariz.; Roy L. Hopfer, Houston, Tex.; Rudolph L. Juliano, Houston, Tex.; Kapil Mehta, Houston, Tex.; Reeta Mehta, Houston, Tex.

[73] Assignee: Board of Regents, The University of Texas System, Austin, Tex.

[21] Appl. No.: 2,455

[22] Filed: Jan. 12, 1987

Related U.S. Application Data

[63] Continuation-in-part of Ser. No. 600,532, Apr. 16, 1984, Pat. No. 4,663,167.

[51] Int. Cl.$^5$ .................... A61K 31/70; A61K 31/685
[52] U.S. Cl. ........................................ 514/31; 514/78; 424/78
[58] Field of Search ............................ 514/78, 37, 31; 424/450

[56] References Cited

U.S. PATENT DOCUMENTS

| | | | |
|---|---|---|---|
| 4,186,183 | 1/1980 | Steck et al. | 424/38 |
| 4,235,871 | 11/1980 | Papahadjopoulos | 424/19 |
| 4,330,534 | 5/1982 | Sakurai et al. | 424/182 |

OTHER PUBLICATIONS

Juliano, Rudy et al. "Pharmacokinetic and Theraputic Consequences of Liposomal Drug Delivery: Fluorodeoxyuridine and Amphotericin B as Examples", vol. 47, *Biologie Cellulaire*, May 1983, pp. 39–46.

Lopez-Berestein et al., "Treatment and Prophylaxis of Disseminated Infection Due to Candida albicans in Mie with Liposome-Encapsulated Amphotericin B", vol. 147, No. 5, *The Journal of Infectious Diseases*, May 1983, pp. 989–945.

Lopez-Berestein et al. "Effects of Sterols on the Therapeutic Efficacy of Liposomal Amphotericin B in Murine Candidiasis", vol. 1, No. 1, *Cancer Drug Delivery*, 1983, pp. 37–42.

Hopfer, R. L., "In Vitro Antifungal Activities of Amphotericin B and Liposome-Encapsulated Amphotericin B", vol. 25, No. 3, *Anti-microbial Agents and Chemotherapy*, Mar. 1984, pp. 387–389.

Mehta, R. et al., "Liposomal Amphotericin B is Toxic to Fungal Cells but not to Mammalian Cells", *Biochimica et Biophysica Acta* 770 (1984) pp. 230–234.

Lopez-Berestein, G. et al.. "Altered Tissue Distribution of Amphotericin B by Liposomal Encapsulation: Comparison of Normal Mice to Mice Infected with Candida albicans", vol. 1, No. 3, *Cancer Drug Delivery*, Jun. 1984, pp. 199–205.

Lopez-Berestein, G. et al., "Prophylaxis of Candida albicans Infection in Neutropenic Mice with Liposome-Encapsulated Amphoterin B", vol. 25, No. 3, *Antimicrobial Agents and Chemotherapy* Mar. 1984.

Lopez-Berestein et al., "Treatment with Liposome-Encapsulated Amphotericin B of Dessiminated Candidiasis in Neutropenic Mice", *Journal of Infectious Diseases*, Aug. 1984.

Graybill, John R. et al., "Treatment of Murine Crptococcosis with Liposome-Associated Amphotericin B", vol. 145, No. 5, *The Journal of Infectious Diseases*, May 1982, pp. 748–752.

Taylor, Robert L., "Amphotericin B in Liposomes: A Novel Therapy for Histoplasmosis".

(List continued on next page.)

Primary Examiner—John W. Rollins
Attorney, Agent, or Firm—Arnold, White & Durkee

[57] ABSTRACT

A method is disclosed for treatment of disseminated fungal infection in a mammal comprising the administration of a fungicidally effective amount of Amphotericin B encapsulated in a substantially sterol-free liposome to the infected mammal. Also provided is an agent for treatment of disseminated fungal infection in a mammal comprising Amphotericin B encapsulated in a liposome which consists essentially of lipids other than sterols.

11 Claims, 2 Drawing Sheets

OTHER PUBLICATIONS

Szoka, Francis Jr. et al., "Comparative Properties and Methods of Preparation of Lipid Vesicles (Liposomes)", *Ann. Rev. Biophys. Bioeng.*, 1980, pp. 467–508.

Tom, Baldwin H., "An Overview: Liposomes and Immunology—Macrophages, Liposomes, and Tailored Immunity", 1980, Liposomes and Immunobiology, pp. 3–19.

Magee, Wayne E. et al., "A Comparison of Negatively and Positively Charged Liposomes Containing Entrapped Polyinosinic Polycytidylic Acid for Interferon Induction in Mice", 451, *Biochimica et Biophysica Acta*, 1976, pp. 610–618.

Graybill ICAAC Abstract, 1982, p. 152.

Tremblay ICAAC Abstract, 1983, p. 222.

Barza ICAAC Abstract, 1983, p. 133.

Fungizone, Product Information, *Physician's Desk Reference* 1983, p. 1929.

HsuChen, Chemical Abstract, vol. 79, 1973 28102g, p. 119.

HsuChen, Chemical Abstract, vol. 80, 1974 23178e, pp. 80–81.

Chen, Chemical Abstract, vol. 87, 1977, 163184y, p. 177.

Sheridan, Chemical Abstract, vol. 87, 1977 195913b, p. 254.

Van Hoogevest, Chemical Abstract, vol. 89, 1978 157215j, p. 23.

Sokolov, Chemical Abstract, vol. 90, 1979 163615b, p. 179.

Boudet, Chemical Abstract, vol. 91, 1979 102345n, p. 80.

Nakamura, Chemical Abstract, vol. 92, 1980, 176122e, p. 208.

Bolard, Chemical Abstract, vol. 93, 1980, 127554j, p. 234.

Takamura, Chemical Abstract, vol. 95, 1981, 161822w, p. 33.

New, Chemical Abstract, vol. 96, 1982, 57652a, p. 360.

Liberman, Chemical Abstract, vol. 78, 1973, 53407e, pp. 106–107.

Kasumov, Chemical Abstract, vol. 79, 1973, 27977s, p. 108.

Gent, Chemical Abstract, vol. 84, 1976, 100974y, p. 185.

Moore, Chemical Abstract, vol. 84, 1976, 146551m, p. 205.

Asher, Chemical Abstract, vol. 87, 1977, 80067m, p. 193.

Schiffman, Chemical Abstract, vol. 87, 1977, 193716r, p. 40.

Borisova, Chemical Abstract, vol. 90, 1979, 82569n, p. 206.

Ohki, Chemical Abstract, vol. 91, 1979, 104067x, p. 251.

Oku, Chemical Abstract, vol. 92, 1980, 123748g, pp. 248–249.

Teerlink, Chemical Abstract, vol. 93, 1980, 142742n, p. 32.

Oehlschlager, Chemical Abstract, vol. 93, 1980, 198021u, p. 85.

Yamaguchi, Chemical Abstract, vol. 93, 1980, 198503c, p. 141.

Babunashvili, Chemical Abstract, vol. 95, 1981, 37636z, p. 272.

Deleers, Chemical Abstract, Vol. 95, 1981, 182480y, p. 219.

Bolard, Chemical Abstract, vol. 96, 1982, 2252q, p. 202.

Aggett, Chemical Abstract, vol. 96, 1982, 81472n, p. 225.

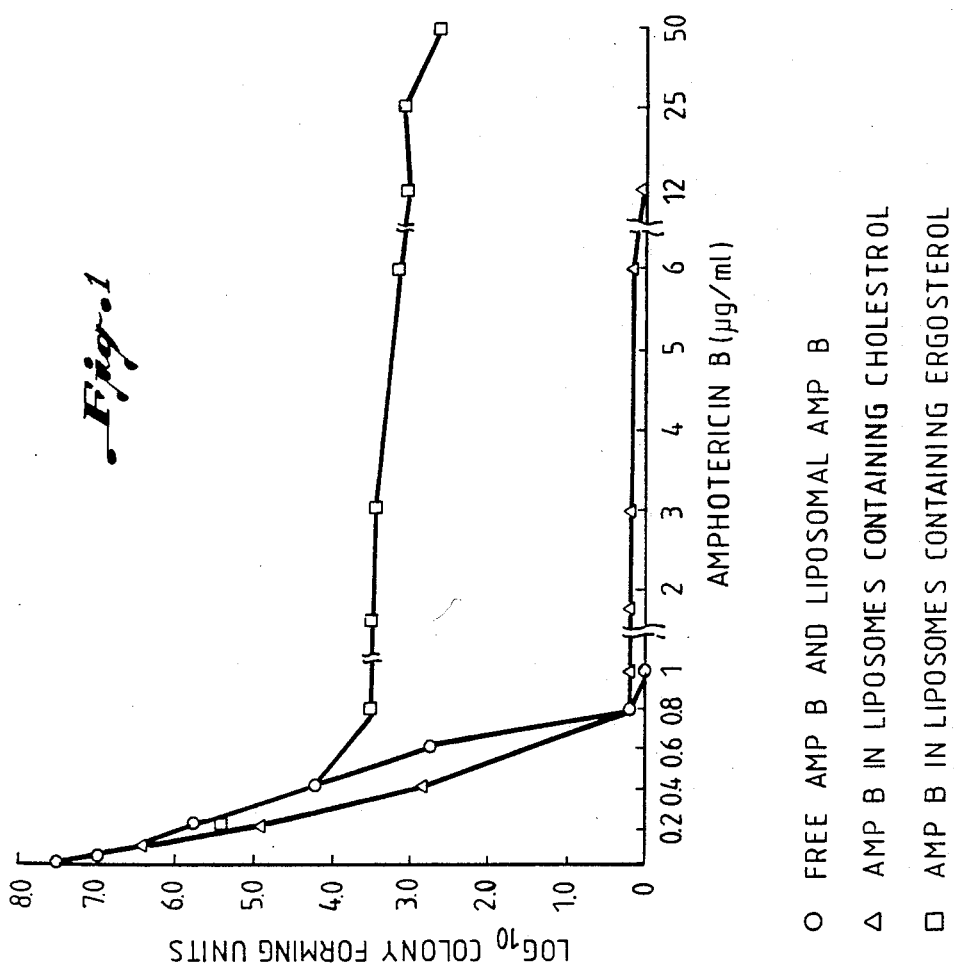

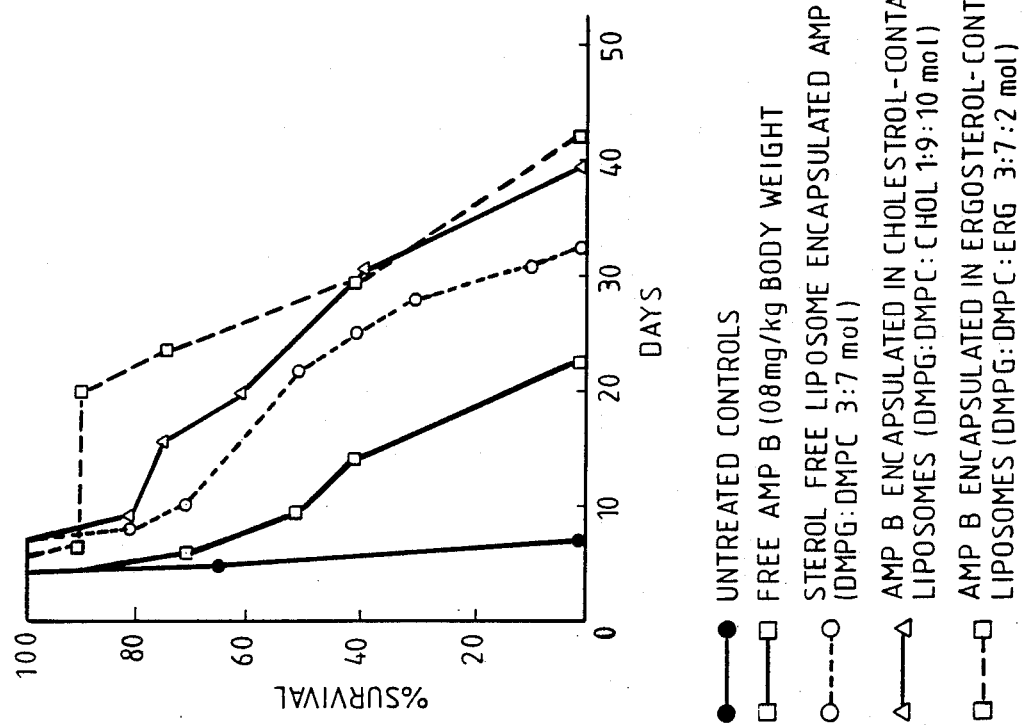
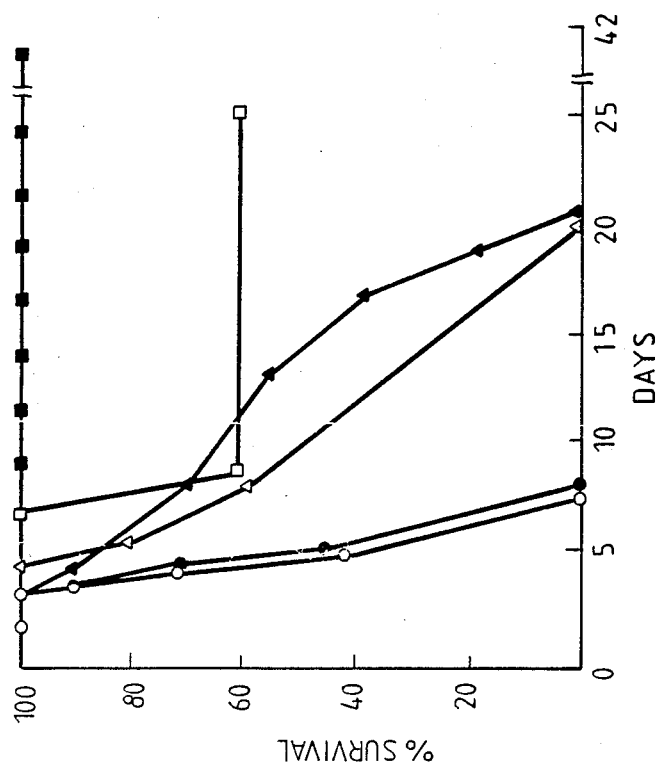

COMPOSITION AND METHOD FOR TREATMENT OF DISSEMINATED FUNGAL INFECTIONS IN MAMMALS

This is a continuation-in-part of Application Ser. No. 600,532, filed on Apr. 16, 1984, now U.S. Pat. No. 4,663,167.

BACKGROUND OF THE INVENTION

The present invention relates to the treatment of disseminated fungal infections in mammals. More particularly, it relates to the use of Amphotericin B, encapsulated within liposomes comprised of lipids other than sterols, as a therapeutic agent for the treatment of disseminated fungal infections in mammals.

Infection is the cause of death in 51% of patients with lymphoma and 75% of patients with leukemia. Although bacteria are the causative organisms of many such infections, fungi account for 13% of the fatal infections in patients with lymphoma and for more than 20% of patients with leukemia. The fungus *Candida albicans* causes more than 80% of these infections, and *Aspergillus spp.* is also a frequent cause of such infections. In addition, fungal infection is a major cause of morbidity and mortality in patients with congenital and acquired deficiencies of the immune system.

Despite the fact that several new antifungal agents have become available, Amphotericin B remains the drug of choice for treatment of most systemic mycoses in cancer and other immuno-compromised patients. Amphotericin B, a polyene antibiotic, is a lipophilic compound which interacts with ergosterol in fungal membranes, thus creating transmembrane channels which permit the escape of many ions and metabolites that are essential to the cell's continued vitality. Unfortunately, the drug also interacts appreciably with the cholesterol found in mammalian cell membranes. This interaction with the cell membrane of mammalian cells is probably the basis of the toxic effects which it exerts on the mammalian kidney, hematopoietic system and central nervous system.

Amphotericin B is insoluble in aqueous solution, consequently it is supplied commercially as a combination of Amphotericin B, desoxycholate and buffers, suspended in a glucose solution to form a colloidal suspension for administration to the patient. It is usually given intravenously over a period of from two to six hours. Faster infusions may result in cardiotoxicity. Other toxic effects of Amphotericin B may manifest themselves as renal dysfunction, anemia, fever and hypotension. Amphotericin B is supplied commercially under the brandname FUNGIZONE® by E. R. Squibb & Sons, Inc. The side effects and contraindications of FUNGIZONE® are discussed at page 1929 et seq. of the Physicians' Desk Reference, 37th Ed. (Oradell, N.J., Medical Economics Co., 1983), hereby incorporated by reference.

The toxicity of Amphotericin B limits the total amount of the drug which may be used in the treatment of a fungal infection. Furthermore, it is often ineffective in neutropenic and immunodeficient patients, patients who are highly susceptible to fungal infections. Consequently, there is a need for a system which decreases the toxicity of Amphotericin B to the mammalian system while simultaneously enhancing its effectiveness against the fungal infection.

It has recently been shown that the encapsulation of certain drugs in liposomes before administration to the patient can markedly alter the pharmacokinetics, tissue distribution, metabolism and therapeutic efficacy of these compounds. ("Liposomes" can be defined as lipid vesicles which are formed spontaneously on addition of an aqueous solution to a dry lipid film.) Further, the distribution and pharmacokinetics of these drugs can be modified by altering the lipid composition, size, charge and membrane fluidity of the liposome in which they are encapsulated.

Recently, liposomes have been used as carriers of Amphotericin B for treatment of murine leishmaniasis (New, R. R. C., et al., "Antileishmanial Activity of Amphotericin and Other Antifungal Agents Entrapped in Liposomes." *J. Antimicrob. Chemother.*, vol. 8 (1981), pp. 371–381), histoplasmosis (Taylor, R. L., et al., "Amphotericin B in Liposomes: A Novel Therapy for Histoplasmosis." *Am. Rev. Respir. Dis.*, vol. 125 (1982), pp. 610–611), cryptococosis (Graybill, J. R., et al., "Treatment of Murine Cryptococosis with Liposome-Associated Amphotericin B." *J. Infect. Dis.*, vol. 145 (1982), pp. 748–752), and candidiasis (Tremblay, C., et al., "Comparative Efficacy of Amphotericin B (AMB) and Liposomal AMB (lip-AMB) in Systemic Candidiasis in Mice." *Abstr.* 1983 *ICAAC.* No. 755 (1983), p. 222). Liposome-encapsulated Amphotericin B has also been used for treatment of coccidioidomycosis in the Japanese macague (Graybill, J. R., et al., "Treatment of Coccidioidomycosis (coccy) in Primates Using Liposome Associated Amphotericin B (Lipo-AMB)." *Abstr.* 1982 *ICCAC,* No. 492 (1982), p. 152).

Administration of Amphotericin B in liposomes provides a more effective method for the treatment of disseminated fungal infections since more of the drug can be given to the infected mammal because of its reduced toxicity.

However, in all above-listed studies, and in all other reported studies of which Applicants are aware (other than their own) in which the composition of the liposomes is given, the liposomes are composed of several lipids, always including at least one sterol. The inclusion of a sterol in the formulation of the liposome was considered essential to the stability of the liposome containing the Amphotericin B. Because it was considered necessary to include a sterol in the lipids making up the liposome, all previous studies of which Applicants are aware were conducted with different proportions or types of sterols in the liposome. These studies represented attempts to define a formulation for optimal stability of the liposome and, simultaneously, increased therapeutic efficacy of Amphotericin B (see, for instance, Barza, M., et al., "Toxicity and Distribution in Mice and Activity In Vitro of Liposomal Amphotericin B (Lip-AMB)." *Abstr.* 1983 *ICCAC,* No. 281 (1983), p. 133 and Tremblay, C., et al., *supra*).

The present invention was made possible by the discovery (1) that sterols are not required to incorporate Amphotericin B into liposomes; (2) that sterols are not essential to the continued stability of an Amphotericin B containing liposome; and (3) that Amphotericin B in sterol-containing liposomes has much less demonstrable in vitro antifungal activity than does Amphotericin B encapsulated in non-sterol containing liposomes. Further, studies have shown that some of the lipids which have been used in the formulation of these Amphotericin B-containing liposomes are themselves toxic. For instance, Graybill, J. R., et al., conducted an experiment (reported in *J. Inf. Dis.* 145; 748 (1983)) in which mice infected with *Cryptococcus neoformans* were treated with liposome-associated Amphotericin B. The liposomes used by Graybill were composed of three complex lipids, sphingomyelin, stearylamine and dicetyl phosphate, and a sterol, ergosterol. It has now been shown that dicetyl phosphate and particularly stearylamine are toxic in mammalian systems in that they cause damage to the liver. Poste, *Biol. Cell* 47; 19 (1983).

Consequently, there is a need for a liposome delivery system for Amphotericin B which is stable and yet easily prepared, requires a minimal amount of lipid per unit of Amphotericin B encapsulated, thereby decreasing the potential toxicity of the lipids in the liposome itself, and which enhances the therapeutic efficacy of Amphotericin B. The present invention is directed to liposome-associated Amphotericin B which offers these advantages in that the liposomes are formulated from lipids other than sterols which were selected for their lack of toxicity to mammals and their ability to encapsulate a greater proportionate amount of Amphotericin B than previous sterol-containing liposome formulations.

SUMMARY OF THE INVENTION

The present invention is directed to a method for the treatment of a disseminated fungal infection in a mammal which involves the administration of a fungicidally effective amount of Amphotericin B, encapsulated in a substantially sterol-free liposome, to the infected mammal. Liposomes with the minimum achievable sterol content (zero if possible) are preferred. The amount of Amp B administered will usually range from about 0.4 mg/kg of body weight to about 4.0 mg/kg.

The present invention also concerns a therapeutic agent for treatment of a disseminated fungal infection in a mammal. The agent comprises Amphotericin B encapsulated within a substantially sterol-free liposome. The liposome consists essentially of one or more compounds selected from the group consisting of phosphoglycerides, phosphatidic acids, and sphingolipids. In another embodiment of the present invention, the compounds can be selected from the group consisting of phosphatidylcholines, phosphatidylserines, phosphatidylglycerols, sphingomyelins, and phosphatidic acids.

BRIEF DESCRIPTION OF THE DRAWINGS

FIG. 1 is a graphical representation of the inhibitory and fungicidal effect of free Amp B and L-Amp B (liposomal Amp B), L-Amp B-C (Amp B in liposomes containing cholesterol) and L-Amp B-E (Amp B in liposomes containing ergosterol) on *C. albicans* 336.

FIG. 2 shows the effect of increasing Amp B concentration in sterol-free liposomes on the survival of mice infected with *C. albicans*.

FIG. 3 shows the effect of lipid composition on the survival of mice infected with *C. albicans* and treated with liposomal Amp. B.

DETAILED DESCRIPTION OF THE INVENTION

The liposome-encapsulated Amphotericin B (Amp B) of the present invention may be prepared by a variety of methods. These methods involve the solubilization of the lipids in an appropriate solvent and the solubilization of Amp B in an appropriate solvent. The Amp B solution is then added to the lipid solution, and the solutions are distributed onto the bottom of a container. The solvent is then removed by evaporation, the lipid-Amp B film is dispersed in a salt solution, and the liposomes allowed to form by shaking.

It will be recognized by those with skill in the art who have the benefit of this disclosure that both the type of lipid and the proportion of that lipid in the liposome may be varied. Applicants have experienced particular success with the phosphoglycerides dimyristoyl phosphatidylcholine (DMPC) and dimyristoyl phosphatidylglycerol DMPG) in a 7:3 DMPC:DMPG molar ratio. This formulation is non-toxic to mammalian systems and is capable of encapsulating 100% of the Amphotericin B available in solution. Combining these same lipids in a 9:1 DMPC:DMPG molar ratio reduces the encapsulation efficiency to 94.9%. Stable Amphotericin B-containing liposomes have been prepared from the phosphoglycerides phosphatidylcholine (PC) and phosphatidylglycerol (PG) in a 9:1 PC:PG ratio. However, liposomes of this formulation were capable of incorporating only 91.8% of the Amphotericin B available in solution.

As used throughout this specification, the term "sterol-free liposome" refers to liposomes comprised of lipid material of a type other than those lipids which may be considered "sterols", for instance, the sterols ergosterol or cholesterol. Other non-sterols, in particular, lipids selected from the phosphoglycerides and the sphingolipids, may be used in the Amp B-containing liposomes of the present invention. Selection of the appropriate lipids for liposome composition is governed by the factors of: (1) liposome stability, (2) encapsulation efficiency, and (3) non-toxicity to mammalian systems. It is expected that one of skill in the art who has the benefit of this disclosure could formulate liposomes according to the present invention which would optimize these factors from, for instance, the phosphoglycerides phosphatidylinositol and cardiolipin, the sphingolipids sphingomyelin and sphingosine, or any combination of these lipids with PC, PG, DMPC or DMPG. Other phosphoglycerides and sphingolipids that might be useful include Egg phosphatidylcholine
Dilauryloylphosphatidylcholine
Dipalmitoylphosphatidylcholine
Distearoylphosphatidylcholine
1-Myristoyl-2-palmitoylphosphatidylcholine
1-Palmitoyl-2-myristoyl phosphatidylcholine
1-Palmitoyl-2-stearoyl phosphatidylcholine
1-Stearoyl-2-palmitoyl phosphatidylcholine
Dioleoylphosphatidylcholine
Dilauryloylphosphatidylglycerol
Dipalmitoylphosphatidylglycerol
Distearoylphosphatidylglycerol
Dioleoylphosphatidylglycerol
Dimyristoyl phosphatidic acid
Dipalmitoyl phosphatidic acid
Dimyristoyl phosphatidylethanolamine
Dipalmitoyl phosphatidylethanolamine
Dimyristoyl phosphatidylserine
Dipalmitoyl phosphatidylserine
Brain phosphatidylserine
Brain sphingomyelin
Dipalmitoyl sphingomyelin
Distearoyl sphingomyelin Several types of liposomes are believed useful for encapsulating Amphotericin B in accordance with the present invention, including stable plural lamellar vesicles and multilamellar liposomes. Whenever "encapsulation" is used in this patent it is meant to include incorporation as well.

The liposome-encapsulated Amp B may then be administered to a mammal infected with a fungal infection. Studies have indicated that the maximum dose of free Amp B tolerated by mice is approximately 0.8 mg/kg of body weight and the $LD_{50}$ is about 1.2 mg/kg. When encapsulated in liposomes, doses of up to approximately 12 mg of Amp B per kg body weight have been shown to result in no gross clinical evidence of toxicity. Nor do such doses cause abnormalities in the serum creatine, blood urea nitrogen and serum glutamic pyruvic transaminase levels of the mice. Histopathology revealed no sign of kidney edema or nephrocalcinosis in mice receiving such doses. Total doses as high as 28 mg/kg of Amp B in liposomes have been given with no apparent acute side effect; no $LD_{50}$ has been identified in the case of liposome-encapsulated Amp B. Comparable doses may be given to humans, again with no apparent toxicological symptoms.

The present invention may be better understood by reference to the following examples.

EXAMPLE 1

Preparation of Liposome-Encapsulated Amphotericin B

The liposome encapsulated Amp B of the present invention may be prepared according to either of the following methods.

The first method is described by Lopez-Berestein, G., et al., "Treatment and Prophylaxis of Disseminated Infection Due to *Candida albicans* in Mice with Liposome-Encapsulated Amphotericin B." *J. Inf. Dis.*, vol. 147 (1983), pp. 939-945, hereby incorporated by reference. Briefly, the method of Lopez-Berestein, et al. involves the preparation of multilamellar vesicles as follows.

The lipids dimyristoyl phosphatidylcholine (DMPC) and dimyristoyl phosphatidylglycerol (DMPG) were obtained from Avanti Polar Lipids (Birmingham, Ala.), and desoxycholate-free Amp B was obtained from Dr. Dan Bonner (Squibb Pharmaceuticals, New Brunswick, N.J.). DMPC and DMPG were dissolved in chloroform in a molar ratio of 7:3 DMPC:DMPG. Amp B was dissolved in methanol at a concentration of 40 µg/ml and the Amp B solution added to the chloroform containing the DMPC and DMPG. This mixture was placed in a rotary evaporator (Rotavapor ®; Brinkman Instruments, Westbury, N.Y.) until all organic solvents were removed. Normal saline was then added and the vesicles formed by gentle agitation. Using this method, to prepare enough liposome-encapsulated Amp B to make up a single dose for a 50 kg patient at a dose of 0.8 mg/kg body weight (as discussed in Example 4) requires the drying of at least 1 to 1.5 liters of the Amp B-methanol solution. Under controlled temperature and pressure conditions, approximately 3 to 4 hours are required to evaporate this volume of the Amp B-methanol solution.

The preferred method for formulation of liposome-encapsulated Amp B in accordance with the present invention is as follows. The lipids DMPC and DMPG and Amp B were obtained from the same sources as described above. The Amp B is dissolved in chloroform in the presence of DMPC and DMPG in a 7:3 molar ratio. All other steps in the preparation of the liposome-encapsulated Amp B were the same as described above.

Using this method, 640 µg of Amp B was dissolved in 1 ml of chloroform (containing 25 mg of the lipid mixture), a significant increase over the 40 µg/ml which can be dissolved in methanol as in the method described above. Consequently, a decreased volume of Amp B solution is required with a concomitant decrease in the amount of time required to evaporate the solution.

EXAMPLE 2

In Vitro Antifungal Activity of Liposome-Encapsulated Amphotericin B

In vitro tests were conducted to determine the effect of free Amp B, Amp B encapsulated in nor-sterol-containing liposomes, (L-Amp B), Amp B encapsulated in cholesterol-containing liposomes (L-Amp B-C) and Amp B in ergosterol-containing liposomes (L-Amp B-E). Desoxycholate free Amphotericin B was obtained from E. R. Squibb & Sons, Inc. Amp B was encapsulated in non-sterol containing liposomes by the method described by Lopez-Berestein, et al., and summarized in Example 1, above. In order to obtain the different doses necessary, lipid concentration was held constant as the Amp B concentration was decreased. The concentration of Amp B within the liposome was determined by scanning in a UV absorption spectrophotometer (Gilford Instrument Laboratories, Oberlin, Ohio) at 405 nm after the Amp B was dissolved in methanol. Cholesterol or ergosterol, obtained from Avanti Polar Lipids (Birmingham, Ala.), was added to the chloroform DMPC:DMPG solution at a molar ratio of 7:3:4 (DMPC:DMPG:sterol).

In vitro activity of free Amp B, L-Amp B, L-Amp B-C and L-Amp B-E was tested on the following yeast species, all clinical isolates obtained from the Clinical Microbiology Laboratories at the University of Texas M.D. Anderson Hospital and Tumor Institute at Houston: *Candida albicans, C. tropicalis, C. parapsilosis, Torulopsis glabrata* and *Cryptococcus neoformans*. The YNB tube dilution method described by Shadomy, S., et al., "Susceptibility Testing with Antifungal Drugs." In Lennette, E. H., et al. (eds.), *Manual of Clinical Microbiology*, 3rd Ed. (Washington, D.C., American Society for Microbiology, 1980), pp. 647-653, hereby incorporated by reference, was used to perform all tests. All tubes were subcultured (10 µl) onto Sabouraud-dextrose agar (SDA) (Scott/Randolph, Houston, Tex.) plates. Minimal fungicidal concentrations (MFC) were determined after incubation for 18 hours. The MFC was defined as the lowest concentration of Amp B that allowed no growth or growth of fewer than four colonies on the subculture plates.

The results are presented in Table 1. These data indicate that the MFC of L-Amp B was increased over that of Amp B in only 8 of the 19 strains tested, and that only in 4 of those 8 strains was the increase significant. The MFC of L-Amp B-C was increased over that of free Amp B in 11 of the strains tested, and in 7 of those strains, this increase was significant. The MFC of L-Amp B-E was higher than that of Amp B in 18 of the 19 strains tested, and the increase was significant in all 18 of those strains. It can be seen that, in terms of the killing of these fungal strains, the efficacy of these compositions may be ranked in decreasing order, with Amp B being most effective, then L-Amp B, L-Amp B-C and, finally L-Amp B-E.

This result was borne out by the killing curve of Amp B, L-Amp B, L-Amp B-C and L-Amp B-E shown in FIG. 1. This curve was constructed by incubation of *C. albicans* strain 336 for 18 hours at 35° C. For these tests, 0.1 ml was removed from all drug concentrations tested. Ten-fold serial dilutions were made, and 0.1 ml of each dilution (in duplicate) was plated onto SDA plates. Colony counts were made after incubation for 48 hours using those dilution plates which grew between 30 and 300 colonies per plate.

TABLE 1

MFC (µg/Amp B/ml) RESULTS USING A VARIETY OF YEAST ISOLATES AND LIPOSOME PREPARATION

| Organisms | Strain | Amp B | L-Amp B | L-Amp B-C | L-Amp B-E |
|---|---|---|---|---|---|
| *Candida albicans* | 306 | 1.6 | 1.6 | 3 | >25* |
| " | 704 | 0.4 | 0.8 | 1.6* | >25* |
| " | 1091 | 0.8 | 0.8 | 1.6 | >25* |
| " | 57 | 0.8 | 0.8 | 0.8 | >25* |
| *Candida tropicalis* | 251 | 3 | 6 | 12* | >25* |
| " | 2463 | 1.6 | 1.6 | 3* | 6* |
| " | 1784 | 3 | 3 | 3 | >25* |
| " | 1324 | 1.6 | 1.6 | 1.6 | >25* |
| *Candida parapsilosis* | 139 | 3 | >25* | >25* | >25* |
| " | 1341 | >25 | >25 | >25 | >25 |
| " | 2300 | 3 | 3 | 3 | >25 |
| *Candida glabrata* | 684 | 3 | 25* | 25* | >25* |
| " | 1905 | 3 | 3 | 3 | 12* |
| " | 2539 | 3 | 3 | 1.6 | 12* |
| " | 1172 | 1.6 | 3 | 1.6 | 6* |
| *Candida neoformans* | 222 | 1.6 | 0.8 | 3 | 25* |
| " | 843 | 0.8 | 12* | 12* | >25* |
| " | 881 | 1.6 | 12* | 12* | >25* |
| " | 595 | 0.4 | 0.8 | 1.6 | 6* |

*Indicates MFC ≧4 fold difference compared to free Amp B.

As shown in FIG. 1, the effect of sterols on growth inhibition was minimal at lower drug concentrations. The sterol-containing liposomes had a protective effect that prevented the killing of fungal cells at higher Amp B concentrations (greater than 1.0 µg/ml). A 12-fold higher concentration of L-Amp-C was required to kill *C. albicans* 336 than either L-Amp B or free Amp B. L-Amp B-E was even less effective in killing *C. albicans* 336 than L-Amp B-C. As shown in FIG. 1, concentrations of 50 µg of Amphotericin B per ml were unable to kill the test organism when administered in ergosterol-containing liposomes.

EXAMPLE 3

In Vivo Antifungal Activity of Liposome-Encapsulated Amphotericin B in Mice

Hale-Stoner mice, 6-8 weeks old and weighing 20-25 g, were obtained from The University of Texas Science Park (Bastrop, Tex.). Mice (10 per group) were injected intravenously with *Candida albicans* strain 336. This strain was grown for 18 hours on SDA plates at 37° C., washed and resuspended in saline. The mice were injected in the tail vein with 0.2 ml of the suspension containing $7 \times 10^5$ colony-forming units. This concentration consistently caused a disseminated infection which, after 48 hours, primarily affected the kidney, liver, spleen and lungs. The mice were injected on the second day of infection with a single dose of Amphotericin B.

Amp B was encapsulated in sterol-free and sterol-containing liposomes prepared by the method described in Example 2, above. Amp B concentration was determined at 405 nm as described in Example 2.

The effect of increasing concentrations of Amp B in sterol-free liposomes on the survival of mice is shown in FIG. 2. In each liposome case shown in FIG. 2, the liposomes contained 400 mg lipid/kg body weight.

Empty liposomes had no significant effect on mouse survival. At doses equivalent to the maximum amount of free Amp B tolerated by mice (0.8 mg/kg body weight), Amp B in non-sterol containing liposomes was as effective as free Amp B in prolonging the survival of infected mice. Increasing the concentration of Amp B in sterol-free liposomes resulted in a highly significant increase in survival time. On day 50 of the infection, 40% of the animals that had received 2 mg Amp B/kg were alive and 100% of the animals that had received 4 mg/kg were alive.

The effect of the lipid composition of the liposome on the survival of mice infected with *C. albicans* 336 was also evaluated. The results are shown in FIG. 3. Each liposome case shown in FIG. 3 used 1.6 mg Amp B in 200 mg total lipid/kg.

Administration of free Amp B improved survival time over the controls (control 50% survival, 5 days, free Amp B 50% survival, 10 days). Amp B encapsulated within liposomes (all animals alive on day 60) significantly enhanced the survival time compared to that of free Amp B (p<0.001, generalized Wilcoxon test). However, in this study there was no significant difference between the survival time of mice treated with Amp B in sterol-free liposomes as compared to the survival time of mice treated with Amp B encapsulated in cholesterol-containing liposomes or ergosterol-containing liposomes.

EXAMPLE 4

Treatment of Systemic Fungal Infections in Cancer Patients with Liposome-Encapsulated Amphotericin B Three cancer patients have been treated for systemic fungal infections with liposome-encapsulated Amphotericin B (Amp B). Amp B was incorporated into multilamellar vesicles as described by Lopez-Berestein, et al., supra (see Example 1). Amp B content was determined by high performance liquid chromatography analysis as described by Nilsson-Ehle, I., et al. "Quantitation of Amphotericin B with Use of High-Pressure Liquid Chromatograph." *J. Infect. Dis.*, vol. 135 (1977), pp. 414-422, hereby incorporated by reference. Phospholipid content was quantified by determining the organic phosphorus in the preparation by the method of Marinetti, G. V. "Chromatographic Separation, Identification, and Analysis of Phosphatides." *J. Lipid Res.*, vol. 3 (1962), pp. 1–20, hereby incorporated by reference. The preparations were sterile as assessed by Bacter and plate culture studies. In all three cases, liposome-encapsulated Amp B was administered to the patients intravenously over 10–15 minutes.

Case 1

A 13-year old female developed diffuse, poorly differentiated lymphocytic lymphoma a number of years ago. She achieved a complete remission following the administration of chemotherapy. Five years later, she was hospitalized with fever, fatigue and general malaise and malignant lymphoid cells were identified in the bone marrow. She was treated with parenteral cyclophosphamide, vincristine and prednisolone. Intrathecal cytosar, hydrocortisone and methotrexate were given prophylactically. After achieving complete remission, maintenance therapy was instituted with 6-mercaptopurine and methotrexate for six months, after which all chemotherapy was stopped.

During that hospitalization, she developed multiple infectious episodes including: typhlitis, *Escherichia coli* and *Staphylococcus aureus* septicemia, bacterial urinary tract infection and herpetic lesions of the skin. In the third month, therapy with Amp B was initiated for persistent fever and *C. albicans* urinary tract infection. After 16 days, 5-fluorocytosine (5FC) was added because of persistent fever. No response was obtained and ketoconazole was administered. In the fifth month, the patient remained febrile. The liver was palpable 4 cm below the right costal margin. She also had cardiomegaly, tachycardia and an $S_3$ gallop. Computerized tomography (CT) of the abdomen showed multiple areas of radiolucency in the liver consistent with fungal abscesses. An open liver biopsy showed infarcted parenchyma and necrotizing abscesses in the liver, due to fungi. No organisms could be cultured from the specimen, but it was morphologically consistent with *Aspergillus spp*. Due to persistence of fever, clinical deterioration and worsening of the liver lesions, hepatic artery infusion with Amp B was started. The patient received a cumulative dose of more than 6 gm Amp B over a seven-month period. Throughout Amp B therapy, fever and chills were observed.

She continued to have a daily temperature of 38.5° C., and remained severely ill, anorectic and malnourished. She had become jaundiced (bilirubin 7 mg/dl). On physical examination of the chest, bilateral basilary rales and a grade II-III apical ejection murmur were detected. The abdomen was distended and diffusely tender, the liver edge was 8 cm below the right costal margin. On chest x-ray examination, there were bilateral pleural effusions, patchy pulmonary infiltrates in both lung fields, and the cardiac silhouette was enlarged. Computerized abdominal tomography showed increased hepatosplenomegaly with increased size of the radiolucencies already observed in the liver, and new lesions were detected in the spleen. Laboratory findings at that time, and during treatment, are summarized in Table 2. Anergy to skin test with recall antigens lymphopenia, an inverted T helper/T suppressor ratio (OKT4/OKT8=16.7/59.7%), and absolute values of T helper of less than 2000 cells/mm$^3$ were observed throughout the course of her disease.

TABLE 2

HEMATOLOGIC, HEPATIC AND RENAL FUNCTION STUDIES DURING LIPOSOMAL-AMPHOTERICIN B THERAPY

| Date | Cumulative Dose of Amphotericin B (mg) | White Blood Cells n/mm$^3$/ Segmented % | BUN mg/100 ml | Creatinine Clearance cc/min | Total Bilirubin mg/100 ml | LDH mu/ml | SGOT mu/ml | Alk. Phosp. mu/ml |
|---|---|---|---|---|---|---|---|---|
| Case 1 | | | | | | | | |
| Before treatment | Baseline | 8.8/9 | 37 | 44 | 7.0 | 256 | 123 | 253 |
| During treatment | 484 | 4.5/29 | 14 | 61 | 0.8 | 134 | 60 | 350 |
| Case 2 | | | | | | | | |
| Before treatment | Baseline | 0.1/0 | 35 | 106 | 2.4 | 222 | 82 | 320 |
| During treatment | 189 | 0.1/0 | 21 | 96 | 0.8 | 183 | 18 | 159 |
| Case 3 | | | | | | | | |
| Before treatment | Baseline | 19.6/88 | 5 | 36 | 0.8 | 277 | 125 | 304 |
| During treatment | 551 | 17.5/72 | 10 | 67 | 0.5 | 193 | 49 | 298 |

Liposomal Amp B (sterol-free) was started at a dose of 0.4 mg/kg intravenously after all other medications were discontinued. No acute side-effects occurred after the first dose. Subsequent therapy was 0.6 mg/kg for 2 doses, and 0.8 mg/kg thereafter. Doses were given every 3 to 4 days for a total of 19 doses (total Amp B 484 mg, total lipid 20 gm). No acute or chronic toxicity was observed during the 3 months of liposomal Amp B treatment. Four weeks after the initial treatment, marked improvement in her general status was reflected by disappearance of fever, increased appetite, improved strength, decreased abdominal pain and hepatomegaly as well as resolution of the lung infiltrates and cardiomegaly. A repeated open liver biopsy performed 4 months after the onset of liposomal Amp B treatment disclosed only areas of fibrosis, and hemosiderosis. No fungal organisms were demonstrated. Six months after discontinuation of treatment, the patient was in excellent general condition.

Case 2

A 22-year old male with acute lymphocyte leukemia had achieved complete remission after induction chemotherapy. Eleven months later, he was found to have recurrent leukemia in the bone marrow. After failing reinduction chemotherapy for four months, he was started on high dose cytosar (3 g/m$^2$/daily×12). He developed a lesion in the nasal turbinate which on biopsy and culture was found to be *Aspergillus terreus*. He received a total of 2.4 gm Amp B intravenously which was always associated with severe nausea, fever and chills.

The nasal lesions worsened in spite of Amp B therapy and new lung lesions appeared on chest x-ray examination which were compatible with typical "fungus balls."

At that time, *A. terreus* was cultured from a lung specimen, bronchial washings and the sputum, urine and stool. The patient developed progressive dypsnea, severe neutropenia, and markedly abnormal liver function tests (Table 2). Anergy to skin tests was observed. He was given a total of 1.4 gm of Amp B by aerosolization without improvement.

Subsequently, sterol-free liposomal Amp B therapy was started at a dose of 0.4 mg/kg with no acute side-effects observed. Doses were repeated at 3-4 day intervals. After the sixth dose, he was afebrile, the nasal lesions had improved and there was clearing of the lung infiltrates on chest x-ray examination Improvement in liver function tests were observed (Table 2). A total of 5 doses of Amp B in liposomes were administered (total Amp B 189 mg, total lipid 5 gm). At that point, liposomal-Amp B therapy was discontinued due to the presence of hallucinations which were later found to be related to the use of several neuroleptic drugs.

Two weeks later, the patient developed new lung infiltrates and clinical evidence of diffuse intravascular coagulation (DIC), which was related to *P. maltophilia* septicemia. Post mortem examination showed evidence of DIC. This was evident by the presence of multiple thrombi in the lungs and kidneys. No fungal organisms were seen in the nose, liver or spleen. Fibrosis was evident in both lungs. Single microscopic foci containing a few fungal organisms were seen in one kidney and in one lung. *P. maltophilia* was cultured from the lung.

Case 3

A 22-year old female was diagnosed of acute progranulocytic leukemia. She was treated with cytosar, daunorubicin, 6-thioguanine, vincristine and prednisone. A bone marrow test conducted one month after initiation of therapy showed a complete remission. Two months after initiation of therapy, she developed cavitary lung infiltrates and necrotizing retinitis. An open lung biopsy was done and the silver stain was positive for budding fungal hyphae. Therapy with Amp B and 5 FC was started. In the following month, she developed right upper quadrant abdominal pain and increased alkaline phosphatase. An abdominal CT scan in the following month showed multiple lesions in the liver and spleen. A liver biopsy showed yeast organisms which were consistent morphologically with Candida. From then on, the patient followed a gradually deteriorating clinical course, requiring continued hospitalization. She was treated with a total of 4 grams of Amp B during her 6-month hospital stay. She was also treated with 5 FC, miconazole and rifampin. A repeated open liver biopsy conducted five months after the abdominal CT scan showed lesions consistent with Candida microabscesses. Throughout this period, the patient continued to spike fevers of 102° F. with rigors.

At this point, the patient looked cachectic and had fever and rigors. An abdominal CT scan showed diffuse parenchymal lesions in the liver and spleen compatible with microabscesses. Sterol-free liposomal-Amp B therapy was started at a dose of 0.4 mg/kg for two doses and continued at 0.8 mg/kg every 72 hours, for a total of 500 mg of Amp B. After two weeks of treatment, the patient showed marked improvement in her clinical condition as evidenced by an increased caloric intake which resulted in discontinuation of IVH. The results of hematologic, hepatic and renal function studies are given in Table 2. She also had decreased abdominal pain and decreased liver span on physical examination. After 3 weeks, she was discharged and therapy was continued as an outpatient. A repeated open liver biopsy done two months after the onset of liposomal Amp B treatment showed no evidence of fungi. The patient continues in good general condition without evidence of chronic toxicity.

EXAMPLE 5

Comparison of Minimal Fungicidal Concentration of Amphotericin B Encapsulated in Different Phospholipid Compositions Several different liposome compositions were tested, using generally the same procedure described in Example 2, to determine the effect of the phospholipids chosen on the minimal fungicidal concentration of Amphotericin B when administered to mice infected with *C. albicans*. The compositions included one or more of the following: DMPC, DMPG, cholesterol (Chol), ergosterol (Erg), and stearylamine (SA). The results are shown in Table 3.

TABLE 3

EFFECT OF LIPID COMPOSITION ON THE MINIMAL FUNGICIDAL CONCENTRATION (MFC) OF LIPOSOMAL-AMPHOTERICIN B

| Lipid Composition | Molar Ratio | MFC ($\mu$g of Amp B per ML) |
|---|---|---|
| Amp B alone | | 1.6 |
| DMPC:DMPG | 7:3 | 1.6 |
| DMPC alone | | 3.2 |
| DMPC:Chol | 9:1 | 3.2 |
| DMPC:Erg | 9:1 | 6.4 |
| DMPG alone | | 50 |
| DMPG:Chol | 9:1 | 50 |
| DMPG:Erg | 9:1 | 50 |
| DMPC:SA | 7:3 | 12.5 |
| DMPC:SA:Chol | 9:1 | 25 |
| DMPC:SA:Erg | 9:1 | 25 |

The above examples are presented for purposes of illustration only, and are not intended to be an exhaustive description of all embodiments of the present invention.

We claim:

1. A therapeutic agent for treating disseminated fungal infection in a mammal, comprising Amphotericin-B encapsulated within a liposome, the liposome being substantially sterol-free and consisting essentially of one or more compounds selected from the group consisting of phosphoglycerides, phosphatidic acids, and sphingolipids.

2. The therapeutic agent of claim 1, where the compounds are selected from the group consisting of phosphatidylcholines, phosphatidylserines, phosphatidylglycerols, sphingomyelins, and phosphatidic acids.

3. The therapeutic agent of claim 1, where the compounds are selected from the group consisting of dimyristoyl phosphatidylcholine, dimyristoyl phosphatidylglycerol, phosphatidylcholine, and phosphatidylglycerol.

4. The therapeutic agent of claim 1, where the liposome is a stable plural lamellar vesicle.

5. The therapeutic agent of claim 1, where the compounds are selected from the group consisting of Egg phosphatidylcholine
Dilauryloylphosphatidylcholine
Dimyristoylphosphatidylcholine
Dipalmitoylphosphatidylcholine
Distearoylphosphatidylcholine
1-Myristoyl-2-palmitoylphosphatidylcholine 1-Palmitoyl-2-myristoyl phosphatidylcholine
1-Palmitoyl-2-stearoyl phosphatidylcholine
1-Stearoyl-2-palmitoyl phosphatidylcholine
Dioleoylphosphatidylcholine
Dilauryloylphosphatidylglycerol
Dimyristoylphosphatidylglycerol
Dipalmitoylphosphatidylglycerol
Distearoylphosphatidylglycerol
Dioleoylphosphatidylglycerol
Dimyristoyl phosphatidic acid
Dipalmitoyl phosphatidic acid
Dimyristoyl phosphatidylethanolamine
Dipalmitoyl phosphatidylethanolamine
Dimyristoyl phosphatidylserine
Dipalmitoyl phosphatidylserine
Brain phosphatidylserine
Brain sphingomyelin
Dipalmitoyl sphingomyelin and
Distearoyl sphingomyelin.

6. A method for treating disseminated fungal infection in a mammal, comprising administering to a mammal a fungicidally effective amount of Amphotericin B encapsulated within a liposome, the liposome being substantially sterol-free and consisting essentially of one or more compounds selected from the group consisting of phosphoglycerides, phosphatidic acids, and sphingolipids.

7. The method of claim 6, where the mammal is a human.

8. The method of claim 6, where the fungicidally effective amount of Amphotericin B is between about 0.4 mg of Amphotericin B per kg of body weight and about 4.0 mg per kg of body weight.

9. The method of claim 6, where the compounds are selected from the group consisting of phosphatidylcholines, phosphatidylserines, phosphatidylglycerols, sphingomyelins, and phosphatidic acids.

10. The method of claim 6, where the compounds are selected from the group consisting of dimyristoyl phosphatidylcholine, dimyristoyl phosphatidylglycerol, phosphatidylcholine, and phosphatidylglycerol.

11. The method of claim 6, where the compounds are selected from the group consisting of
Egg phosphatidylcholine
Dilauryloylphosphatidylcholine
Dimyristoylphosphatidylcholine
Dipalmitoylphosphatidylcholine
Distearoylphosphatidylcholine
1-Myristoyl-2-palmitoylphosphatidylcholine
1-Palmitoyl-2-myristoyl phosphatidylcholine
1-Palmitoyl-2-stearoyl phosphatidylcholine
1-Stearoyl-2-palmitoyl phosphatidylcholine
Dioleoylphosphatidylcholine
Dilauryloylphosphatidylglycerol
Dimyristoylphosphatidylglycerol
Dipalmitoylphosphatidylglycerol
Distearoylphosphatidylglycerol
Dioleoylphosphatidylglycerol
Dimyristoyl phosphatidic acid
Dipalmitoyl phosphatidic acid
Dimyristoyl phosphatidylethanolamine
Dipalmitoyl phosphatidylethanolamine
Dimyristoyl phosphatidylserine
Dipalmitoyl phosphatidylserine
Brain phosphatidylserine
Brain sphingomyelin
Dipalmitoyl sphingomyelin and
Distearoyl sphingomyelin.

* * * * *

UNITED STATES PATENT AND TRADEMARK OFFICE
CERTIFICATE OF CORRECTION

| | | |
|---|---|---|
| PATENT NO. | : 4,978,654 | |
| APPLICATION NO. | : 07/002455 | |
| DATED | : December 18, 1990 | |
| INVENTOR(S) | : Gabriel Lopez-Berestein et al. | |

It is certified that error appears in the above-identified patent and that said Letters Patent is hereby corrected as shown below:

In Column 1, between lines 9 and 10, please insert --This invention was made with government support under grant number BRSG RR5511 awarded by the National Institutes of Health. The government has certain rights in the invention.--.

Signed and Sealed this

Twenty-fifth Day of December, 2007

JON W. DUDAS
*Director of the United States Patent and Trademark Office*